United States Patent [19]
Quinn

[11] Patent Number: 5,704,786
[45] Date of Patent: Jan. 6, 1998

[54] CHUCK WITH A PUSH BUTTON RELEASE FOR A DENTAL/MEDICAL DEVICE

[75] Inventor: Michael J. Quinn, Wildwood, Mo.

[73] Assignee: Young Dental Manufacturing Company, Earth City, Mo.

[21] Appl. No.: 648,817

[22] Filed: May 16, 1996

[51] Int. Cl.⁶ ................................................. A61C 1/14
[52] U.S. Cl. .................................. 433/128; 279/76
[58] Field of Search ........................... 433/127, 128; 279/76, 79

[56] References Cited

U.S. PATENT DOCUMENTS

| | | | |
|---|---|---|---|
| 3,413,578 | 11/1968 | Dennison | 335/167 |
| 4,014,099 | 3/1977 | Bailey | 433/128 |
| 4,370,132 | 1/1983 | Wohlgemuth | 433/128 |
| 4,398,886 | 8/1983 | Schuss et al. | 433/128 |
| 4,661,062 | 4/1987 | Seigneurin | 433/128 |
| 4,975,056 | 12/1990 | Eibofner | 433/84 |
| 5,028,181 | 7/1991 | Jenkins et al. | 409/215 |
| 5,037,299 | 8/1991 | Nakanishi | 433/128 |
| 5,090,906 | 2/1992 | Pernot | 433/128 |

FOREIGN PATENT DOCUMENTS 2905484  8/1979  Germany ........................ 433/127

*Primary Examiner*—John J. Wilson
*Attorney, Agent, or Firm*—Polster, Lieder, Woodruff & Lucchesi

[57] ABSTRACT

A medical/dental device is provided which includes a body having a hollow sleeve and a head at an end of the sleeve. The head defines an upwardly opening chamber which receives a chuck. The chuck includes a bur tube which removably receives a medical/dental tool of the latch-shaft type and a push button actuator to release the shaft from the bur tube. The bur tube includes a flexible arm which extends above the bur tube's upper surface and has an inwardly extending finger positioned to engage the groove of the shaft. The push button includes a downwardly extending pedestal which engages the arm to move the arm from a first position in which the groove and the finger create an interference fit to prevent the shaft from being removed from the head to a second position in which the finger is disengaged from the groove to allow removal of the shaft.

30 Claims, 4 Drawing Sheets

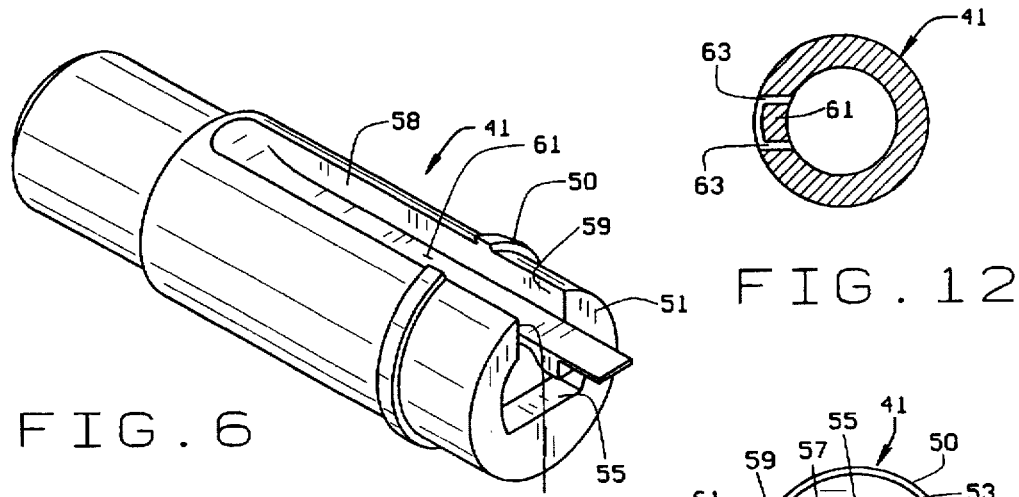
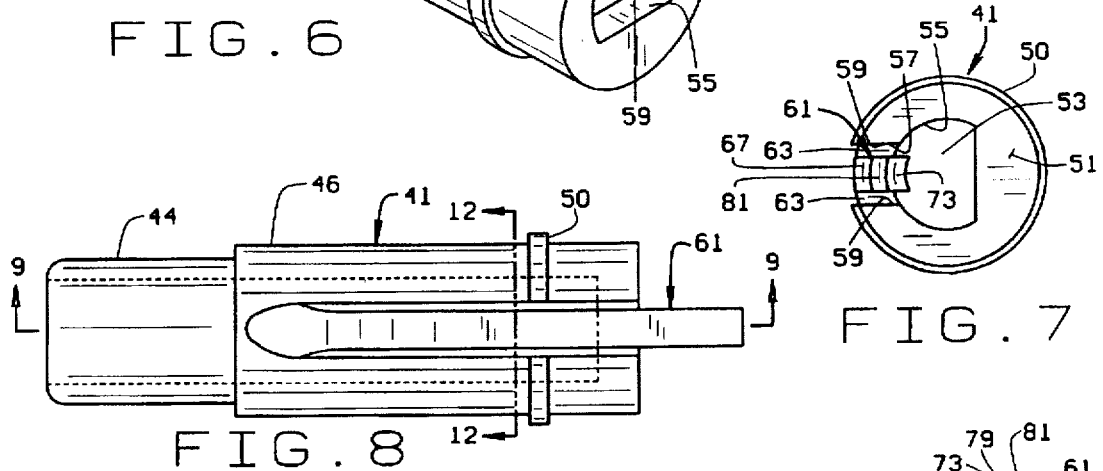
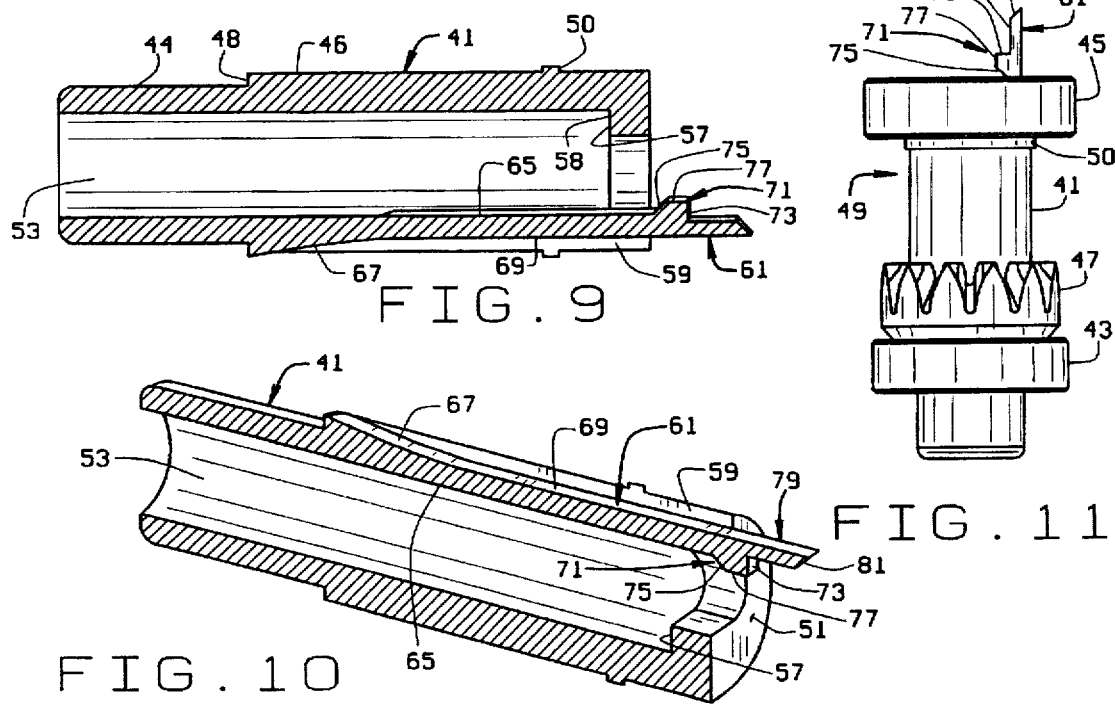

CHUCK WITH A PUSH BUTTON RELEASE FOR A DENTAL/MEDICAL DEVICE

BACKGROUND OF THE INVENTION

This invention relates to medical/dental handpieces, and in particular to a chuck of a medical/dental handpiece which removably receives tools having latch-type shafts and which has a push button release to allow easy removal of the tool from the handpiece. Dental handpieces include both high speed turbine types (typically 200,000 to 400,000 rpm) having an air motor and gear-driven lower speed types (typically, 1,000 to 30,000 rpm) having an air motor or an electrical motor. Both have long employed chucks for releasably holding dental burs which cut, grind and polish teeth. Similar burs are used in surgery for performing these functions on bone. Because the shafts of dental tools are quite small and quite closely toleranced (latch-type shaft diameters are typically between 0.0919" and 0.0925"), and because the demands of dental and surgical procedures require the utmost performance, chucks are high precision devices requiring a great deal of care and expense in their manufacture.

There are essentially two types of shafts that are provided on dental/medical burs. One is a generally straight smooth shaft which is typically frictionally held by the chuck. This is sometimes referred to as a friction grip shaft and is made in accordance with ANSI/ADA spec. No.23 for a Class 4 bur. The other is a shaft having a groove formed near its top end and is referred to as a latch-type shaft. This is a Class 2 bur. In handpieces which accept latch-type shafts, the handpiece typically includes a bar or lever in the top of the handpiece head which swings horizontally relative to the sleeve of the handpiece (when the handpiece is held with the bur extending downwardly). The lever includes a slot which engages the groove in the bur shaft to hold the bur in the handpiece. When the lever is swung outwardly from the sleeve of the handpiece, the lever's slot is disengaged from the groove in the shaft of the latch bur. The bur may then be removed from the handpiece. The formation of the lever in the head requires that a slot be formed in the head. This creates an opening into the head which will allow contaminants and debris to enter the head. Such contaminants and debris are difficult to fully clean from the handpiece. The debris can include items such as dental matter, amalgam, bone, etc. If the debris is not cleaned from within the head of the handpiece, it will abrade the gears which drive the bur, and substantially shorten the working life of the handpiece. Further, if the contaminants (such as saliva, blood, etc.) are not properly cleaned from the handpiece, the handpiece will not be properly sterilized.

SUMMARY OF THE INVENTION

One object of the present invention is to provide a simple, effective chuck for releasably holding a dental tool in a handpiece.

Another object is to provide a release mechanism for the chuck which is easy to operate.

Another object is to provide such a release mechanism which substantially seals the head against the entry of debris into the head.

Another object is to provide such a chuck which is easy to construct and economical to produce.

These and other objects will become apparent to those skilled in the art in light of the following disclosure and accompanying drawings.

In accordance with the invention, generally stated, a medical/dental device is provided which includes a body having a hollow sleeve and a head at an end of the sleeve. The sleeve receives a drive mechanism. The head defines an upwardly opening chamber having an upwardly opening mouth and a floor. An opening is formed in the floor and is sized to admit the passage of a shaft of a medical/dental instrument. The medical/dental instrument is of the type wherein the shaft has an axis, an axially extending flat extending downwardly from a top of the shaft and a groove spaced from the top of the shaft which is perpendicular to the flat. The groove is defined by upper and lower surfaces and at least the groove upper surface is perpendicular to the axis of the shaft. A bur tube is received in the head chamber. The bur tube includes a bur tube body having a top surface and a bore which extends through the body sized to receive the shaft. The top surface includes a "D" hole which opens into the bur tube bore. The "D" hole is sized to receive the flat of the shaft to rotationally fix the shaft relative to the bur tube such that rotation of the bur tube will rotatably drive the shaft. The shaft is sized so that the groove is spaced above the bur tube upper surface. The bur tube includes a flexible arm which extends above the upper surface of the bur tube and has an inwardly extending finger positioned below the top of the arm to engage the shaft groove. The arm is movable between a first position in which the groove and the finger create an interference fit to prevent the shaft from being removed from the head and a second position in which the finger is disengaged from the groove to allow removal of the bur.

A cap or ring is received in the mouth of the head and has an upper opening. A push button actuator is received in the cap for axial movement relative to the cap and extends through the cap upper opening to be operable by a user of the medical/dental device. The push button actuator includes a top, an annular wall depending from the top, and a pedestal depending from the push button top inside of the annular wall. The push button is selectively movable between a first position in which the pedestal is spaced from the upper portion of the bur robe arm and a second position in which the pedestal engages the upper portion of the bur tube arm to move the arm from the arm's first position to the arm's second position. The push button is biased to its first position, preferably by a deformable silicone disk, although a spring or spring washer could also be used.

The pedestal defines a truncated cone and has a sloped side. The bur tube arm has a sloped upper surface which is engaged by the sloped side of the pedestal when the push button is pressed. Preferably, the sloped side of the pedestal has a length greater than the sloped surface of the arm upper portion. When the push button is pressed, the sloped side of the pedestal engages the sloped surface of the arm to move the arm between the first and second positions. A bore or depression is formed in the lower surface of the pedestal and is sized to prevent the top surface of the bur shaft from contacting the pedestal when the push button is moved to its second position.

A slot is formed in the wall of the bur tube and extends downwardly from a top of the wall. The arm is positioned in the slot, extends upwardly from the bottom of the slot, and, preferably, is integrally formed with the bur tube. Preferably, the slot extends through the wall of the bur tube such that an inner surface of the arm defines a portion of an inner surface of the bur tube. The arm has a thickness which, at least in pan, is narrower than the bur tube wall. The arm can be divided into three portions. At the bottom of the arm, at the bottom of the slot, the arm has a thickness substantially equal to the thickness of the bur tube wall. Above this first portion, the arm has a thickness that is narrower than the width of the bur tube wall. This second portion of the arm extends to the finger. The outer surface of the arm includes a curved area which forms the transition between the first and second portions of the arm. Above the finger, the arm has a thickness narrower than the second portion of the arm.

The finger has a flat upper surface and a sloped lower surface which are joined by a generally vertical wall. At the base of the finger, where the finger is attached to the arm, the finger has a height that is approximately equal to the height of the groove in the shaft of the dental/medical tool. The flat upper surface of the finger is adjacent the flat or horizontal upper surface of the shaft when the finger is engaged with the groove. Thus, the shaft cannot be removed when the finger is engaged with the groove. The shaft has a beveled edge at the top thereof which interacts with the sloped lower surface of the finger to urge the finger and the arm radially outwardly when the bur shaft is inserted into the bur tube. The arm snaps from the second position to the first position when the groove comes into alignment with the finger.

BRIEF DESCRIPTION OF THE DRAWINGS

FIG. 6 is a perspective view of a bur tube of the chuck;

FIG. 7 is a top plan view of the bur tube;

FIG. 8 is a side elevational view of the bur tube;

FIG. 9 is a cross-sectional view of the bur tube taken along line 9—9 of FIG. 8;

FIG. 10 is a perspective cross-sectional view of the bur tube;

FIG. 11 is an elevational view of a bur tube assembly which includes the bur tube; and FIG. 12 is a cross-sectional view of the bur tube taken along line 12—12 of FIG. 8.

Description of the Preferred Embodiment

Figure 1:
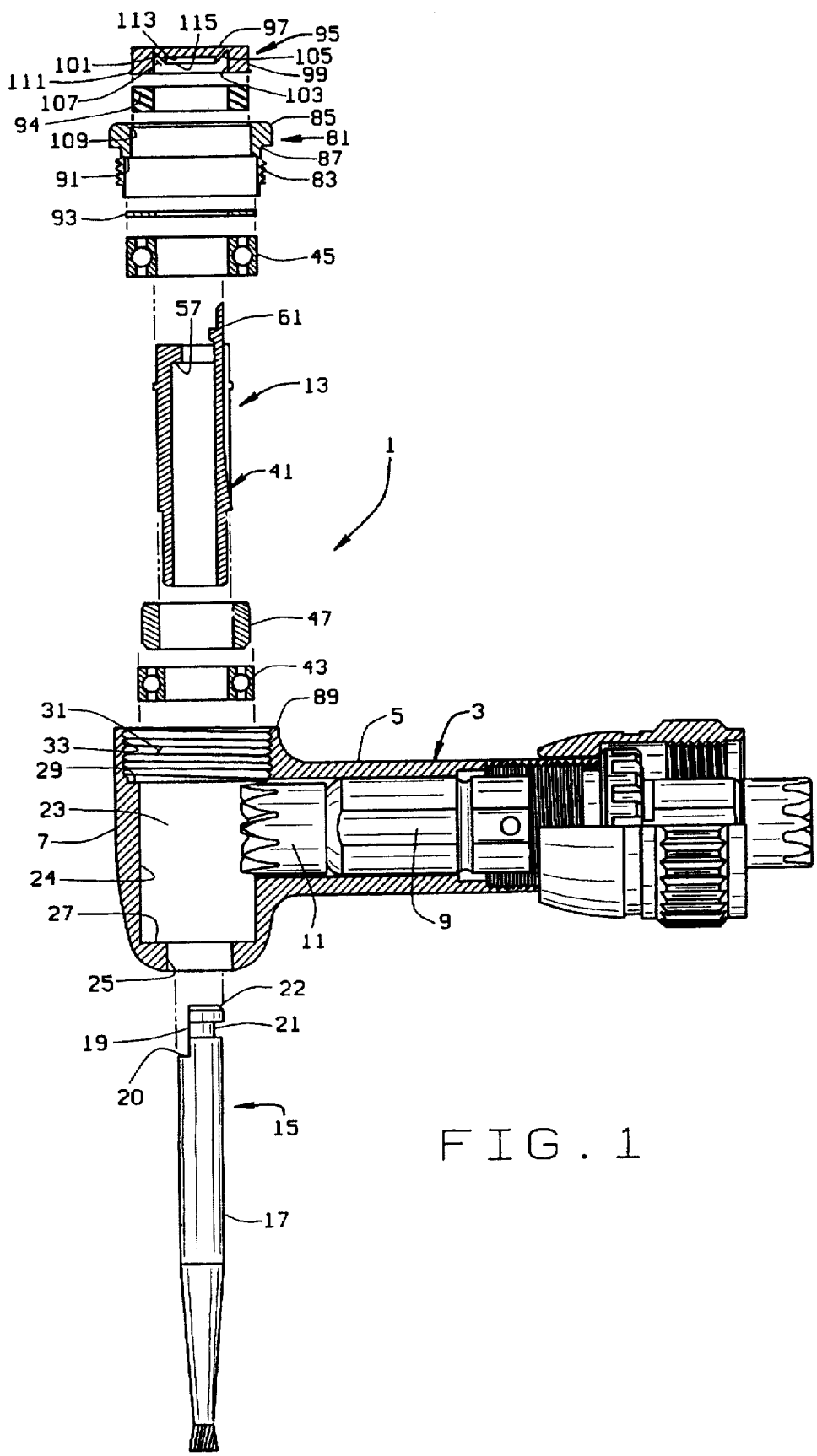
FIG. 1 is an exploded view of a handpiece including a chuck of the present invention.

A handpiece 1 of the present invention is generally shown in FIGS. 1–5. The handpiece 1 includes a body 3 having a hollow sleeve 5 and a hollow head 7. The sleeve 5 receives a drive member 9 having a drive gear 11 at the end thereof. The handpiece 1 is mounted on a handpiece drive and the drive member 9 is operatively connected to the handpiece drive to be rotationally driven by the handpiece drive. A chuck 13 is received in the head 7 of the handpiece 1. Chuck 13 receives a bur 15 which has a shaft 17. As best seen in FIG. 1, the shaft 17 has an axially extending flat 19 extending down from a top surface of the shaft. The shaft has a shoulder 20 at the bottom of the flat 19. A groove 21 is formed near the top of the shaft 17 spaced from the shoulder 20. The groove is generally perpendicular to the axis of the shaft and to the flat 19, and is defined by upper and lower surfaces. The top surface of the shaft preferably has a beveled or rounded edge 22.

The head 7 of the handpiece 1 defines an upwardly opening chamber 23 defined by a generally cylindrical wall 24 which receives the chuck 13. An opening 25 is formed in the floor 27 of the chamber. Opening 25 is sized to receive the shaft 17. Near the top of the head 7, the wall 24 is stepped, as at 29, to define an area 31 having an internally threaded wall 33. The wall 33 has a greater diameter than the wall 24.

The chuck 13 includes a bur tube 41 and a push button actuator 95. The bur tube 41 is journaled in a bottom bearing 43, a top bearing 45, and a driven gear 47. The bearings 43 and 45 and the driven gear 47 are all generally annular and are press-fit onto the bur tube 41. The bur tube 41, bearings 43 and 45, and driven gear 47 form a bur tube assembly 49 (FIG. 11).

The bur tube 41 is shown in detail in FIGS. 6–10. The bur tube 41 includes a lower section 44 which has an outer diameter sized to be press fit in the lower bearing 43 and an upper section 46 which has an outer diameter sized to be press fit in the driven member 47 (such as a gear or a turbine) and the upper bearing 45. Alternatively, the driven member could be laser welded to, or integrally formed with, the bur tube 41. The bur tube's lower section 44 has a smaller diameter than the upper section 46, and the two sections define a step or shoulder 48. The shoulder 48 provides a stop to prevent the lower bearing 43 from being pressed too far onto the bur tube 41. As can be seen in FIG. 11, when the gear 47 is pressed onto the bur tube, the gear is adjacent the top of the lower bearing 43. A ring or shoulder 50 is formed around the upper section 46 spaced from the top 51 of the bur tube 41. The ring 50 provides a seat on which the upper bearing 45 sits when the bearing 45 is press fit on the bur tube 41.

Figure 2:
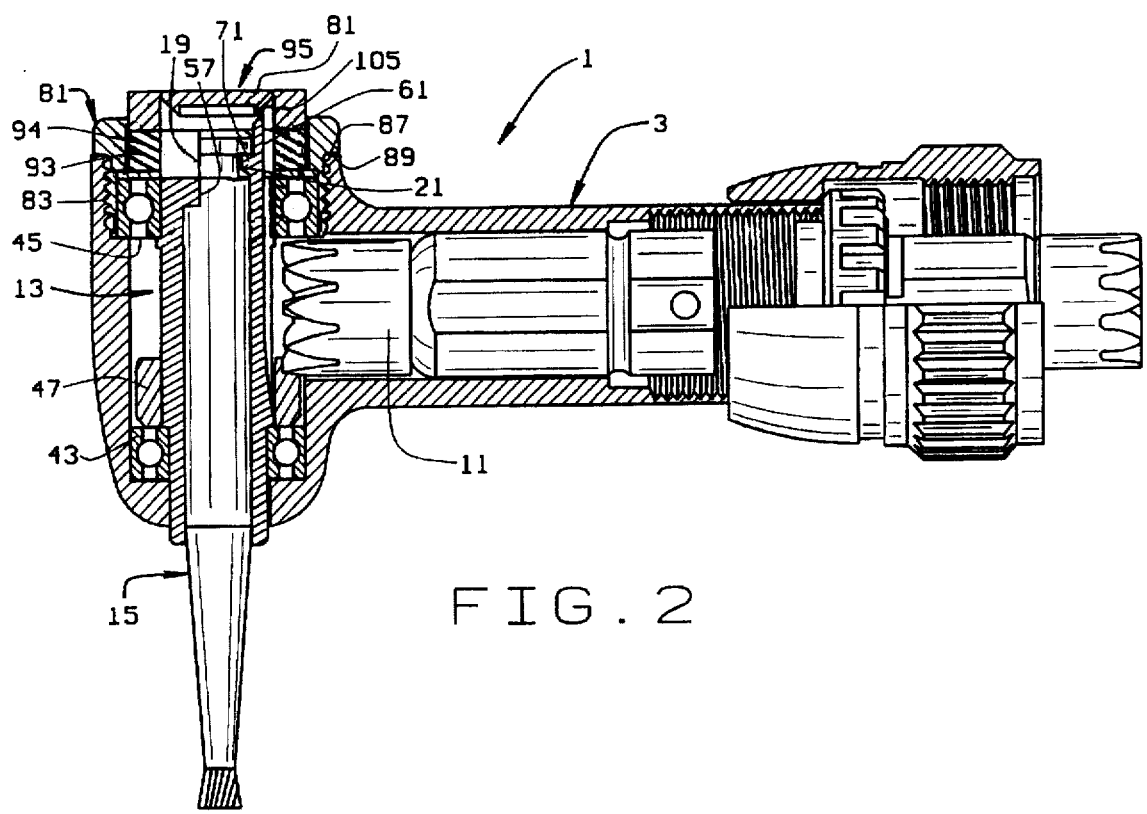
FIG. 2 is a cross-sectional view of a handpiece, the chuck securely holding a bur therein for use.

A cylindrical bore or passage 53 of substantially constant diameter extends through the bur tube 41 and is partially closed by the top 51 of the bur tube. The bore 53 is sized to slidably receive the shaft 17 of the bur 15. The top 51 of the tube has a "D" hole 55 which partially closes the bore 53. As seen in FIGS. 9 and 10, the "D" hole 55 creates a ledge 57 at the top of the bore 53. The ledge 57 has an inner or lower surface 58. As seen in FIG. 2, the surface 20 of bur shaft 17 abuts the inner surface 58 of the ledge 57 when the bur is fully received in the bur tube 41. The flat 19 extends through the "D" hole 55 and the flat 19 and the "D" hole 55 interact to rotationally fix the bur 15 with respect to the bur tube 41. Thus, when the bur tube is rotated, the bur 15 will also rotate.

An elongate slot 58 (FIG. 6) is formed in the bur tube upper section 46. The slot 58 is defined by side walls 59 and extends from the top of the bur tube nearly to the bur tube shoulder 48. A flexible arm 61 extends the from the base of the slot up past the top 51 of the bur tube 41. The arm 61 has a circumferential width that is less than the circumferential width of the slot 58. The arm 61 thus defines spaces or gaps 63 (FIG. 7) with the side walls 59 of the slot 58. The arm 61 has a inner surface 65 and an outer surface. The inner surface is shaped to match the curvature of the bur tube's inner surface. At the base of the arm, the arm has a thickness equal to the thickness of the bur tube wall. The outer surface curves radially inwardly, as at 67, from the base of the arm for a short distance. The outer surface of the arm then becomes generally straight, as at 69, where the thickness of the arm is about ½ the thickness of the wall of the bur tube 41. The arm 61 is formed integrally with the bur tube 41, such that the bur tube and arm 61 form a one-piece, unitary component of the handpiece.

An inwardly directed finger 71 is spaced from the top of the arm 61 and above the top 51 of the bur tube 41. The finger 71 is preferably integrally formed with the arm 61. The finger 71 has a flat upper surface 73 and a sloped lower surface 75 connected by a generally vertical side surface 77. The finger 71 is sized to be received in the groove 21 of the bur shaft 17, as seen in FIG. 2 when the shaft is inserted in the bur tube to secure the shaft in the handpiece 1. As also seen in FIG. 2, the height of the finger, at the base of the finger, is about equal to the height of the shaft groove 21. The side surface 77, at the end of the finger, has a height equal to about ½ to ¾ of the height of the groove 21. The finger is spaced beneath the top of the arm 61, and the portion 79 of the arm 61 which extends above the finger 71 is thinner than the remainder of the arm and has a sloped top surface 81.

The opening 31 of the head 7 receives a generally cylindrical and open cap or ring 81 which has an externally threaded stem 83. The stem 83 is screwed into the opening 31 of the head to secure the cap 81 to the head. The cap has an outwardly extending flange 85 which forms a shoulder 87 with the stem 83. When the cap 81 is screwed into the head 7, the cap shoulder 87 is adjacent the top surface 89 of the head 7, as seen in FIG. 2. The inner diameter of the stem 83 is sufficiently wide to receive the upper bearing 45. The cap 81 includes an inner shoulder 91 at the top of the stem 83. As seen in FIG. 2, a washer 93 is disposed between the top surface of the upper bearing 45 and the cap's inner shoulder 91. A spring 94 is positioned on the washer 93. The spring 94 is preferably a washer of a compressible material, such as silicone. The spring 94, however, could also be a spring washer or a spiral spring. The washer 93 has an outer diameter sized so that the washer 93 is captured between the cap shoulder 91 and the upper bearing 45.

The cap 81 receives a push button actuator 95 which extends up out of the cap 81 and slides axially with respect to the cap. The push button 95 has a generally flat top 97, an annular wall 99, and an internal pedestal 101 extending downwardly from the inner surface of the cap top 97. The pedestal 101 is concentric with the wall 99. The cap wall 99 has a generally circular inner surface 103. The pedestal forms a truncated cone and has an upwardly and radially outwardly sloped side surface 105 which intersects the inner surface 103 at the top thereof. The surface 105 and wall 99 define a generally triangularly shaped area 107.

The cap has a small inwardly extending lip 109 and the push button has a outwardly extending flange 111 at the base of its wall 99. The cap lip 109 and push button flange 111 cooperate to maintain the push button 95 in the cap 81 so that the push button 95 does not come out of the cap 81. The silicone disk 94, which is received in the cap 81, operates to bias the push button actuator 95 normally upwardly.

The operation of the chuck 13 is shown in FIGS. 2-5. In FIG. 2, the handpiece is shown in its operating condition. The finger 71 of the flexible arm 61 is received in the groove 21 of the bur shaft 17. The flat top surface 73 of the finger 71 is adjacent the flat top surface of the groove 21. The groove 21 and finger 71 create an interference fit to prevent the bur 15 from being pulled out of the handpiece 1. In this operating position, the top surface 81 of the bur robe arm 61 is spaced from the pedestal 101 of the push button 95.

Figure 3:
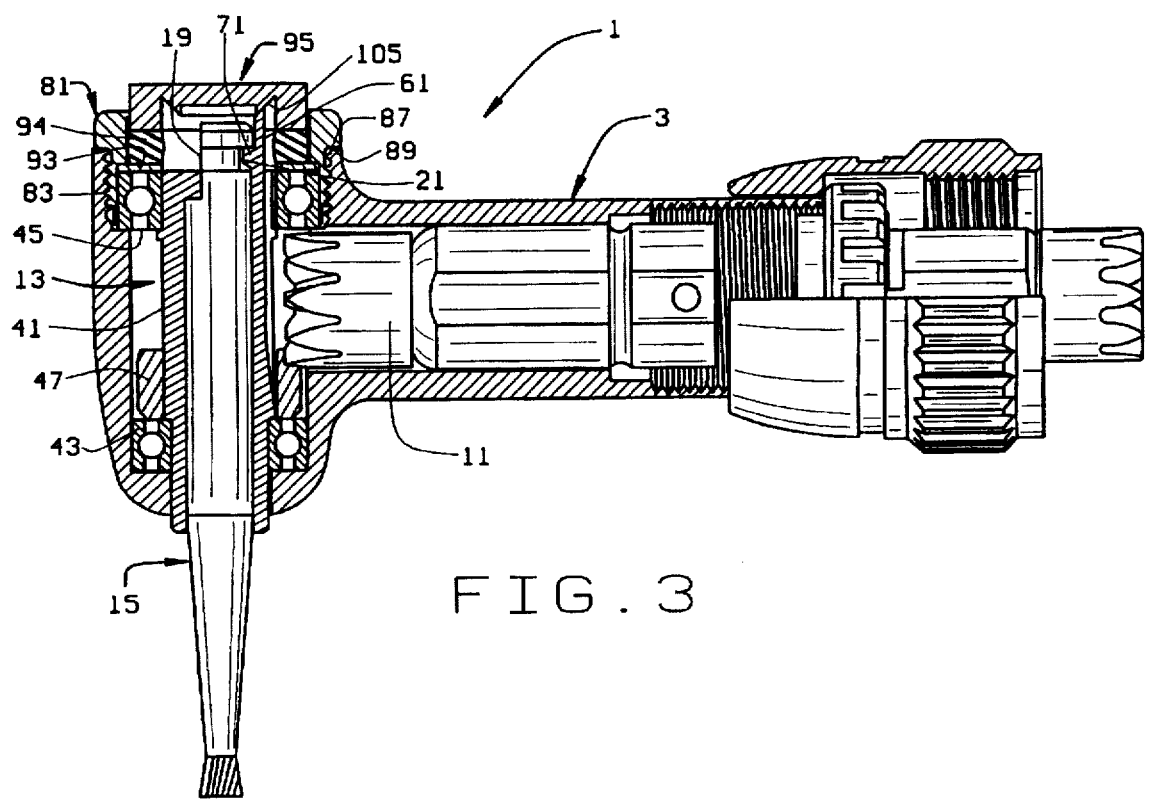
FIGS. 3–5 are similar to the view of FIG. 2, but show the operation of a push button release mechanism of the chuck to easily remove the bur from the handpiece.

In FIG. 3, the push button actuator 95 is shown pushed downwardly to a point where the sloped surface 105 of the pedestal 101 is in contact with the sloped surface 81 of the bur robe arm 61. As can be seen, the surfaces 105 and 81 have complimentary slopes so that they will slide against one another. Further, the pedestal surface 105 is longer than the arm surface 81 so that the arm 61 does not fill the space 107 between the pedestal 101 and the inner surface 103 of the push button wall 99. The surfaces 81 and 105 can thus slide against each other.

Figure 4:
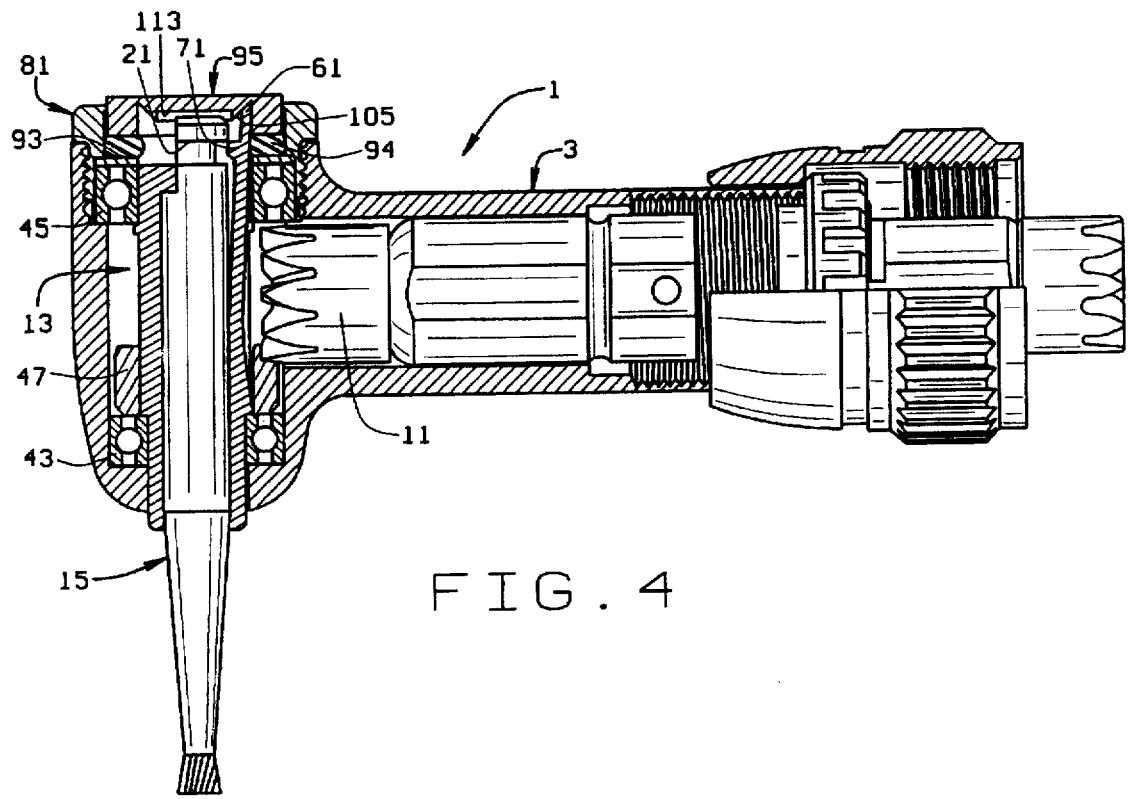
Figure 5:
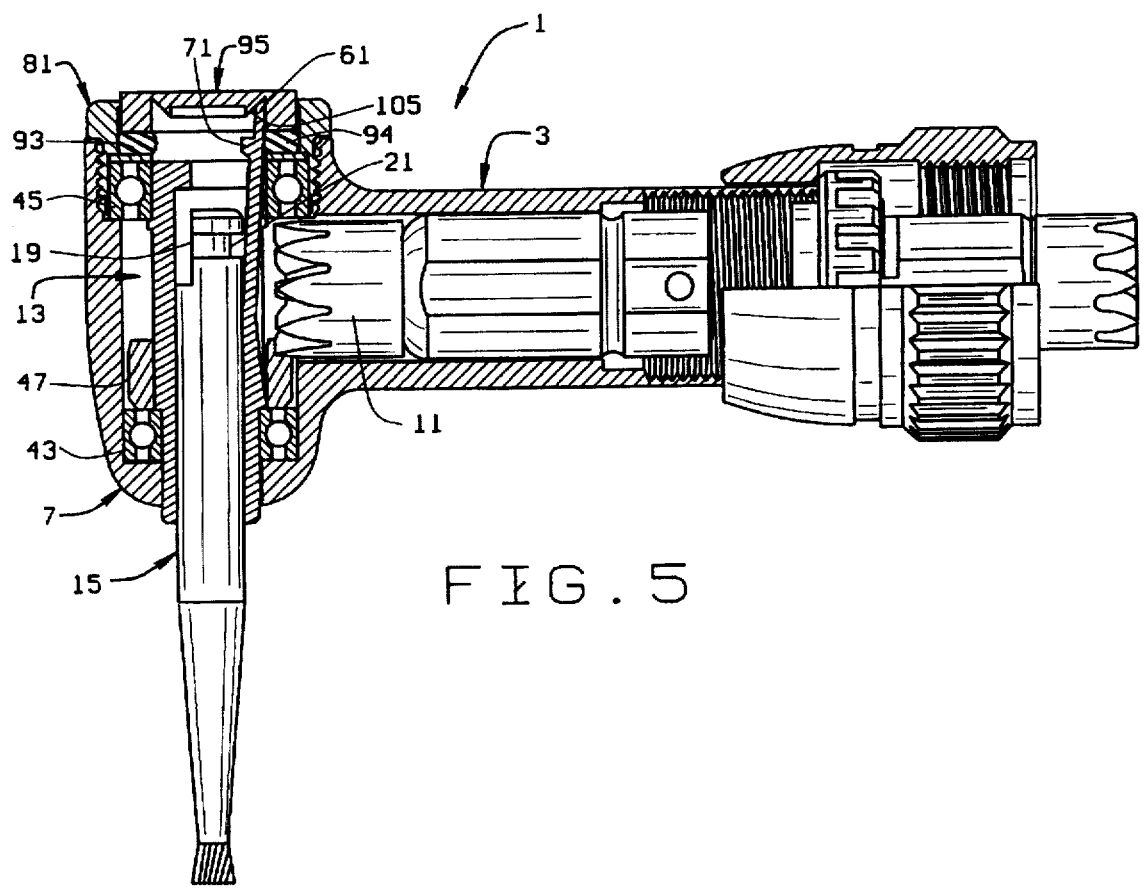

In FIG. 4, the push button actuator 95 is pushed down farther. When the push button is continued to be pushed down, as shown in FIG. 4, the interaction of the surfaces 81 and 105 cause the pedestal to push the arm 61 radially outwardly to move the finger 71 out of the shaft groove 21. The pedestal surface 105 and the finger 71 are sized such that when the push button 95 is fully depressed, the finger 71 will be fully disengaged from the groove 21 of the bur 15. When the finger 71 is disengaged from the bur groove 21, the bur may be pulled out of the handpiece head 7, as shown in FIG. 5.

As can be seen (in FIGS. 1-5), the pedestal 101 has a bore 113 formed in its lower surface 115. The bore 113 is sized in diameter and depth to receive the top of the bur shaft 17 to prevent the bur shaft 17 from contacting the bottom of the pedestal 101. If the bottom of the pedestal were to contact the top of the bur shaft, the finger may not be able to be fully disengaged from the groove 21. This result could also be achieved by other means, for example by changing the sizes of the arm portion 79 above the finger 71 and the push button 95.

To insert a bur into the head 7, the bur shaft is simply pushed into the head. The beveled or curved edge of the shaft will interact with the sloped surface 75 of the finger 71 and push the finger radially outwardly as the shaft is urged past the finger. When the groove 21 comes into alignment with the finger 71, the arm 61 will spring back and the finger 71 will engage the groove 21 to secure the bur 15 in the handpiece 1. Although the bur may need to be rotated to pass the flat of the bur through the "D" hole 53, the operation of the chuck 13 allows for the bur to be inserted into the chuck without the need to depress the push button 95. There is thus no latch, button, or other mechanism that need be actively operated by the dentist, as is required by the chucks presently available, to secure latch-type bur shafts in the chuck.

The thinness of the arm 61 provides resiliency to the arm and creates an arm that does not need undue force to be flexed outwardly. If the arm 61 had a thickness as thick as the wall of the bur tube 41, the chuck would be more difficult to operate. Further, the narrowing of the arm prevents the arm from contacting the inner race of the upper beating 45. As can be appreciated, the bearing 45 surrounds the bur tube 41. If the arm 61 were as thick as the bur tube wall, the arm would not be able to be deflected outwardly, and the chuck thus would not be operable to either accept or release a bur.

In manufacturing the bur tube, the distance between the bottom surface 58 of the ledge 57 and the top surface 73 of the finger 71 is important. This distance must be closely toleranced to match the distance between the upper surface of the shaft's groove 21 and the shoulder 20 of the shaft. If the distance between the ledge surface 58 and finger top surface 73 is too short, the shoulder 20 will not bear against the bottom of the ledge 57, and the shaft will have too much axial play or end play. If the distance between the surfaces 58 and 73 is too great, the shoulder 20 will seat against the surface 58 before the finger 71 engages the groove 21, and the bur will not be secured in the chuck 13. Similarly, the height of the finger 71, at its root, should be substantially equal to the height of the groove 21.

As can be appreciated, the chuck provided by the present invention securely holds a latch-type bur shaft in a handpiece so that the bur may be driven by the handpiece. The push button release of the chuck is easy to operate. Further, the push button 95 and cap 81 effectively seal or close the head 7 of the handpiece. There are no openings or gaps large enough through which debris can enter the head of the handpiece. The effective life of the handpiece will not be reduced, as occurs with handpieces currently available. The push button and cap also substantially prevent contaminants, such as saliva, from entering the head. If such contaminants do enter the head, the handpiece can be sterilized, such as in an autoclave.

As variations within the scope of the appended claims may be apparent to those skilled in the art, the foregoing description is set forth only for illustrative purposes and is not meant to be limiting. For example, the gear 47 could be replaced with a turbine and the drive 9 and the drive gear 11 can be replaced with a system for delivering operating air to the head such that the bur would be air driven rather than gear driven. The arm need not be as long as the upper portion of the bur tube. The arm need only be long enough to allow it to be sufficiently flexible to move between a position in which its finger engages the shaft groove and a position in which the finger is disengaged from the shaft groove. The slot in which the arm is positioned need not extend completely through the wall of the bur tube. The arm could be of a uniform depth, and there could be a step between the arm and the base of the slot, instead of the sloped surface 67. The sloped surface 81 of the arm 61 could be replaced with a sharp corner or edge, and this edge would then be contacted by the sloped surface of the pedestal. Alternatively, the pedestal could have a sharp edge and the arm could include the sloped surface 81. In these variations, the arm will be urged outwardly by the interaction of a sloped surface and an edge or corner. Although the flat on the bur shaft and the "D" hole in the bur tube are preferred to rotationally fix the bur shaft with respect to the bur tube, other means could be used. The shaft could simply be frictionally held in place. Alternatively, the bur shaft and bur tube could have axially extending fibs and grooves which cooperate to rotationally fix the bur shaft in the bur tube so that the shaft is rotated by the bur robe. The bur robe is describe to have a "D" hole. This "D" hole could be replaced with any opening have a straight, for example a hexagonal or octagonal head. The opening in the top of the bur robe need only be shaped complementary to the shape of the top of the bur shaft to prevent the bur shaft from rotating relative to the bur robe. These examples are merely illustrative.

I claim:

1. A medical/dental device including:
   a body having a hollow sleeve and a head at an end of said sleeve, said sleeve receiving a drive mechanism, said head defining an upwardly opening chamber, said chamber having an upwardly opening mouth and a floor having an opening therethrough sized to admit the passage of a shaft of a medical/dental instrument, said shaft having an axis and a groove perpendicular to said axis and spaced from a top of said shaft, said groove being defined by upper and lower surfaces, at least said groove upper surface being perpendicular to the axis of said shaft;
   a chuck which removably receives said shaft, said chuck including a one-piece, unitary bur tube which is rotatably received in said head and a push button actuator, said shaft being receivable in said bur tube to be rotationally fixed relative to said bur tube to be driven by rotation of said bur tube;
   a cap received in the mouth of said head; and
   a driven mechanism on said bur tube, said driven mechanism being rotatably driven by said drive mechanism to rotate said bur tube and said bur;
   said one-piece unitary bur tube including a bur tube body having a wall, an upper surface, and a bore which extends through said body sized to removably receive said shaft; an upper portion of said shaft being extendible above said upper surface of said bur tube to space said shaft groove above said bur tube upper surface; said bur tube further including an axially extending flexible arm formed in said body wall; said arm extending above said bur tube upper surface, said flexible arm including an inwardly extending finger positioned to engage said shaft groove when said shaft is inserted in said bur tube, said arm being movable between a first position in which said finger is received in said groove to prevent said shaft from being removed from said head and a second position in which said finger is disengaged from said groove to allow removal of said bur; an upper portion of said arm extending above the top of said shaft when the medical/dental instrument is received in said device;
   said push button actuator being received in said cap and extending through said cap upper opening to be operable by a user of said medical/dental device, said push button actuator including a top, an annular wall depending from said top and having an inner surface, and a member depending from said push button top inside of said annular wall; said push button being axially slideable in said cap between a first position in which said member is spaced from said upper portion of said bur tube arm and a second position in which said member engages said upper portion of said bur tube arm to move said arm from said arm first position to said arm second position.

2. The medical/dental device of claim 1 wherein said push button member comprises a pedestal, the pedestal defining a truncated cone, said pedestal having a sloped side which engages said bur tube arm upper portion to move said bur tube arm from its first position to its second position.

3. The medical/dental device of claim 1 wherein the bur tube bore is of substantially constant diameter.

4. The medical/dental device of claim 1 wherein at least a portion of said flexible arm is narrower than the wall of said bur tube body.

5. A medical/dental device including:
   a body having a hollow sleeve and a head at an end of said sleeve, said sleeve receiving a drive mechanism, said head defining an upwardly opening chamber, said chamber having an upwardly opening mouth and a floor having an opening therethrough sized to admit the passage of a shaft of a medical/dental instrument, said shaft having an axis and a groove perpendicular to said axis and spaced from a top of said shaft, said groove being defined by upper and lower surfaces, at least said groove upper surface being perpendicular to the axis of said shaft;
   a chuck which removably receives said shaft, said chuck including a bur tube which is rotatably received in said head and a push button actuator, said shaft being receivable in said bur tube to be rotationally fixed relative to said bur tube to be driven by rotation of said bur tube;
   a cap received in the mouth of said head and having an upper opening; and
   a driven mechanism on said bur tube, said driven mechanism being operatively connected to said drive mechanism to be rotatably driven by said drive mechanism to rotate said bur tube and said bur;
   said bur tube including a bur tube body having an upper surface and a bore which extends through said body sized to removably receive said shaft; an upper portion of said shaft being extendible above said upper surface of said bur tube to space said shaft groove above said bur tube upper surface; said bur tube further including a flexible arm extending above said bur tube upper surface, said flexible arm including an inwardly extending finger positioned to engage said shaft groove when said shaft is inserted in said bur tube, said arm being movable between a first position in which said finger is received in said groove to prevent said shaft from being removed from said head and a second position in which said finger is disengaged from said groove to allow removal of said bur; an upper portion of said arm extending above the top of said shaft;

said push button actuator being received in said cap and extending through said cap upper opening to be operable by a user of said medical/dental device, said push button actuator including a top, an annular wall depending from said top and having an inner surface, and a pedestal depending from said push button top inside of said annular wall; said push button being axially slideable in said cap between a first position in which said pedestal is spaced from said upper portion of said bur tube arm and a second position in which said pedestal engages said upper portion of said bur tube arm to move said arm from said arm first position to said arm second position, said push button pedestal defining a truncated cone, said pedestal having a sloped side which engages said bur tube arm upper portion to move said bur tube arm from its first position to its second position, said bur tube arm upper portion having a sloped upper surface, said sloped side of said pedestal engaging said sloped surface of said arm upper portion.

6. The medical/dental device of claim 5 wherein said shaft includes a flat extending axially from a top of said shaft and said bur tube body top surface including a hole having at least one flat edge which opens into said bur tube bore, said hole being sized to receive said flat of said shaft to rotationally fix said shaft relative to said bur tube such that rotation of said bur tube will rotatably drive said shaft.

7. The medical/dental device of claim 5 wherein said driven mechanism is a driven gear and said drive mechanism is a drive gear, said drive and driven gears meshing to rotationally drive said bur tube.

8. The medical/dental device of claim 5 wherein said flexible arm is integrally formed with said bur tube.

9. The medical/dental device of claim 5 wherein said sloped side of said pedestal has a length greater than the sloped surface of said arm upper portion.

10. The medical/dental device of claim 5 wherein said bur tube has a wall and a slot extending downwardly from a top of said wall, said arm being positioned in said slot.

11. The medical/dental device of claim 10 wherein said slot extends through said wall of said bur tube such that an inner surface of said arm defines a portion of an inner surface of said bar tube.

12. The medical/dental device of claim 10 wherein said arm has a width which is narrower than said slot and a depth, for at least a part thereof, which is narrower than the width of a wall of said bur tube.

13. The medical/dental device of claim 12 wherein said slot has a bottom, said arm extending from the bottom of said slot, said arm having a thickness, at the bottom of said slot, substantially equal to the thickness of the bur tube wall.

14. The medical/dental device of claim 13 wherein the arm has an outer surface, said outer surface being curved to define a transition between a first portion of said arm where said arm has a thickness equal to the approximately width of said bur tube wall and a second portion of said arm where said arm has a thickness narrower than the bur tube wall.

15. The medical/dental device of claim 12 wherein the arm includes a third portion which extends above said finger, said arm third portion having a thickness narrower than the thickness of said arm second portion.

16. The medical/dental device of claim 5 wherein said finger has a flat upper surface and a sloped lower surface, said upper and lower surfaces being interconnected by a generally vertical wall.

17. The medical/dental device of claim 16 wherein said shaft has a top edge which is beveled or rounded, said top edge of said shaft interacting with the sloped lower surface of said finger to urge said finger and said arm radially outwardly when said bur shaft is inserted into said head, said arm snapping from said second position to said first position when said groove comes into alignment with said finger.

18. The medical/dental device of claim 5 wherein said driven mechanism is mechanically connected to said drive mechanism to be rotated thereby.

19. A medical/dental device including:

a body having a hollow sleeve and a head at an end of said sleeve, said sleeve receiving a drive mechanism, said head defining an upwardly opening chamber, said chamber having an upwardly opening mouth and a floor having an opening therethrough sized to admit the passage of a shaft of a medical/dental instrument, said shaft having an axis and a groove perpendicular to said axis and spaced from a top of said shaft, said groove being defined by upper and lower surfaces, at least said groove upper surface being perpendicular to the axis of said shaft;

a chuck which removably receives said shaft, said chuck including a bur tube which is rotatably received in said head and a push button actuator, said shaft being receivable in said bur tube to be rotationally fixed relative to said bur tube to be driven by rotation of said bur tube;

a cap received in the mouth of said head and having an upper opening; and a driven mechanism on said bur tube, said driven mechanism being operatively connected to said drive mechanism to be rotatably driven by said drive mechanism to rotate said bur tube and said bur;

said bur tube including a bur tube body having an upper surface and a bore which extends through said body sized to removably receive said shaft; an upper portion of said shaft being extendible above said upper surface of said bur tube to space said shaft groove above said bur tube upper surface; said bur tube further including a flexible arm extending above said bur tube upper surface, said flexible arm including an inwardly extending finger positioned to engage said shaft groove when said shaft is inserted in said bur tube, said arm being movable between a first position in which said finger is received in said groove to prevent said shaft from being removed from said head and a second position in which said finger is disengaged from said groove to allow removal of said bur; an upper portion of said arm extending above the top of said shaft;

said push button actuator being received in said cap and extending through said cap upper opening to be operable by a user of said medical/dental device, said push button actuator including a top, an annular wall depending from said top and having an inner surface, and a pedestal depending from said push button top inside of said annular wall; said push button being axially slideable in said cap between a first position in which said pedestal is spaced from said upper portion of said bur tube arm and a second position in which said pedestal engages said upper portion of said bur tube arm to move said arm from said arm first position to said arm second position; said pedestal having a lower surface, a bore being formed in said lower surface, said bore having a diameter at least as great as the diameter of said bur shaft at the top of said shaft and a depth sufficiently deep to prevent the top surface of said bur shaft from contacting said pedestal when said push button is moved to its second position.

20. A chuck for a medical/dental device, the medical/dental device removably receiving a tool having a shaft, said shaft having an axis and a groove spaced from the top of said shaft, said groove being defined by upper and lower surfaces, at least said groove upper surface being perpendicular to the axis of said shaft; the chuck including a bur tube which removably receives said shaft and a push button actuator operable to move said bur tube from a first position in which said bur tube interacts with said groove of said shaft to secure said tool in said medical/dental device and a second position in which said tool may be removed from said medical/dental device;

said bur tube including a body having wall, a top surface, an axially extending flexible arm formed in said wall and extending above said top surface, said arm having a top surface and a finger spaced below said arm top surface, said finger being snappingly received in said groove of said tool shaft to secure said tool in said medical/dental device, said finger having a flat upper surface which interferes with said groove upper surface to prevent said tool from being removed from said shaft when said bur tube is in said first position and said finger is engaged in said groove;

said push button actuator including a top and a pedestal depending from said top, said pedestal having a sloped side wall, said push button actuator being axially slideable relative to said bur tube between a first position in which said sloped side wall of said pedestal is spaced from said top surface of said arm, and a second position in which said sloped side wall of said pedestal engages said top surface of said arm to urge said arm outwardly a distance sufficient to disengage said arm finger from said shaft groove.

21. A chuck for a medical/dental device, the medical/dental device removably receiving a tool having a shaft, said shaft having an axis and a groove spaced from the top of said shaft, said groove being defined by upper and lower surfaces, at least said groove upper surface being perpendicular to the axis of said shaft; the chuck including a bur tube which removably receives said shaft and a push button actuator operable to move said bur tube from a first position in which said bur tube interacts with said groove of said shaft to secure said tool in said medical/dental device and a second position in which said tool may be removed from said medical/dental device;

said bur tube including a body having a top surface, a flexible arm extending above said top surface, said arm having a top surface and a finger spaced below said arm top surface, said finger being snappingly received in said groove of said tool shaft to secure said tool in said medical/dental device, said finger having a flat upper surface which interferes with said groove upper surface to prevent said tool from being removed from said shaft when said bur tube is in said first position and said finger is engaged in said groove;

said push button actuator including a top and a pedestal depending from said top, said pedestal having a sloped side wall, said push button actuator being axially slideable relative to said bur tube between a first position in which said sloped side wall of said pedestal is spaced from said top surface of said arm, and a second position in which said sloped side wall of said pedestal engages said top surface of said arm to urge said arm outwardly a distance sufficient to disengage said arm finger from said shaft groove; said top surface of said arm being sloped, said slope of said arm top surface corresponding to the slope of said pedestal sloped side wall.

22. The chuck of claim 21 wherein said bur tube has a wall and a slot extending downwardly from a top of said bur tube wall, said arm being positioned in said slot, said arm extending from a bottom of said slot.

23. The chuck of claim 22 wherein said arm has a first portion near said bottom of said slot which has a depth approximately equal to the width of said bur tube wall, a second portion above said first portion which has a depth less than the width of said wall, and a third portion above said arm finger which has a depth less than the depth of said second portion.

24. The chuck of claim 23 wherein said arm has an outer surface, said outer surface having a curved portion, said curved portion of said outer surface extending between said first and second portions of said arm.

25. A medical/dental device including:

a body having a hollow sleeve and a head at an end of said sleeve, said sleeve receiving a drive mechanism, said head defining an upwardly opening chamber having a floor and an opening in said floor sized to admit the passage of a shaft of a medical/dental instrument, said shaft having an axis and a groove perpendicular to said axis spaced from a top of said shaft, said groove being defined by upper and lower surfaces, at least said groove upper surface being perpendicular to the axis of said shaft;

a chuck which removably receives said shaft, said chuck including a bur tube which is rotatably received in said head, said shaft being received in said bur tube to be rotationally fixed relative to said bur tube to be driven by rotation of said bur tube;

a driven mechanism on said bur tube, said driven mechanism being rotatably driven by said drive mechanism to rotate said bur tube and said shaft;

said bur tube including a bur tube body having a wall, an upper surface, and a bore which extends through said body sized to receive said shaft; an upper portion of said shaft extending above said upper surface of said bur tube to space said shaft groove above said bur tube upper surface; said bur tube further including an axially extending flexible arm formed in said bur tube body wall; said arm extending above said bur tube upper surface, said flexible arm including an inwardly extending finger positioned to engage said shaft groove and a portion extending above said finger, said finger having a flat upper surface and a sloped lower surface, said arm being movable between a first position in which said finger is received in said shaft groove to prevent said shaft from being removed from said head and a second position in which said finger is disengaged from said groove to allow removal of said shaft;

said shaft having a top edge which is beveled or rounded, said top edge of said shaft interacting with the sloped lower surface of said finger to urge said finger and said arm radially outwardly when said shaft is inserted into said head, said arm snapping from said second position to said first position when said groove comes into alignment with said finger.

26. The medical dental device of claim 25 wherein the chuck further includes a push button actuator, said upwardly opening chamber defining a mouth, said push button actuator being received in said mouth of said chamber; said push button actuator including a top, an annular wall depending from said top and having an inner surface, and a pedestal depending from said push button top inside of said annular wall; said push button being axially slideable in said cap between a first position in which said pedestal is spaced from said upper portion of said bur tube arm and a second position in which said pedestal engages said upper portion of said bur tube arm to move said arm from said arm first position to said arm second position.

27. The medical/dental device of claim 26 wherein said push button is biased to its first position.

28. The medical/dental device of claim 27 wherein said push button is biased by a deformable silicone disk.

29. A medical/dental device including:
 a body having a hollow sleeve and a head at an end of said sleeve, said sleeve receiving a drive mechanism, said head defining an upwardly opening chamber, said chamber having an upwardly opening mouth and a floor having an opening therethrough sized to admit the passage of a shaft of a medical/dental instrument, said shaft having an axis and a groove perpendicular to said axis and spaced from a top of said shaft;
 a chuck which removably receives said shaft, said chuck including a one-piece, unitary bur tube which is rotatably received in said head and a push button actuator, said shaft being receivable in said bur tube to be rotationally fixed relative to said bur tube to be driven by rotation of said bur tube; and
 a driven mechanism on said bur tube, said driven mechanism being rotatably driven by said drive mechanism to rotate said bur tube and said bur;
 said one-piece unitary bur tube including a bur tube body having a wall, a bore which extends through said body sized to removably receive said shaft; an axially extending flexible arm formed in said body wall; said flexible arm including an inwardly extending finger positioned to engage said shaft groove when said shaft is inserted in said bur tube, said arm being movable radially between a first position in which said finger is received in said groove to prevent said shaft from being removed from said head and a second position in which said finger is disengaged from said groove to allow removal of said bur;
 said push button actuator being received in said head; said push button actuator having an upper surface which is exposed eternally of said head to be pushed by an operator of the medical/dental device; said push button actuator including a member depending from an inner surface of said push button; said push button being slidable axially relative to said head between a first position in which said member is spaced from said bur tube arm and a second position in which said member engages said bur tube arm to move said arm from said arm first position to said arm second position.

30. The medical/dental device of claim 29 wherein an upper portion of said bur tube arm extends above the top of said shaft when the medical/dental instrument is received in said device, said member of said push button cap engaging said upper portion of said bur tube arm to move said arm from said arm's first position to said arm's second position.

* * * * *

UNITED STATES PATENT AND TRADEMARK OFFICE
CERTIFICATE OF CORRECTION

PATENT NO. : 5,704,786
DATED : January 6, 1998
INVENTOR(S) : Michael J. Quinn

It is certified that error appears in the above-identified patent and that said Letters Patent is hereby corrected as shown below:

Column 2, line 40, replace the word "robe" with the word --tube--;
Column 2, line 65, replace the word "pan" with the word --part--;
Column 4, line 9, replace the word "beatings" with the word --bearings--;
Column 4, line 14, replace the word "beating" with the word --bearing--;
Column 4, line 29, replace the word "beating" with the word --bearing-- (appearing twice in that same line);
Column 5, line 56, replace the word "robe" with the word --tube--;
Column 5, line 61, replace the word "robe" with the word --tube--;
Column 6, line 42, replace the word "beating" with the word --bearing--;
Column 7, line 28, replace the word "comer" with the word --corner--;
Column 7, line 33, replace the word "fibs" with the word --ribs--;
Column 7, line 35, replace the word "robe" with the word --tube-- (appearing twice in that same line);
Column 7, line 38, replace the word "robe" with the word --tube--;
Column 7, line 41, replace the word "robe" with the word --tube--.

Signed and Sealed this

Fourteenth Day of April, 1998

Attest:

BRUCE LEHMAN

Attesting Officer

Commissioner of Patents and Trademarks